(12) United States Patent
Thibaut et al.

(10) Patent No.: US 7,425,530 B2
(45) Date of Patent: Sep. 16, 2008

(54) STEREOSELECTIVE PREPARATION OF CYCLIC L-AMINO ACIDS

(75) Inventors: Denis Thibaut, Paris (FR); Volker Döring, Paris (FR); Philippe Marliere, Etiolles (FR)

(73) Assignee: Rhodia Chimie, Aubervilliers (FR)

(*) Notice: Subject to any disclaimer, the term of this patent is extended or adjusted under 35 U.S.C. 154(b) by 0 days.

(21) Appl. No.: 10/479,719

(22) PCT Filed: Jun. 10, 2002

(86) PCT No.: PCT/FR02/01983

§ 371 (c)(1),
(2), (4) Date: May 26, 2004

(87) PCT Pub. No.: WO02/101003

PCT Pub. Date: Dec. 19, 2002

(65) Prior Publication Data

US 2005/0038255 A1    Feb. 17, 2005

(30) Foreign Application Priority Data

Jun. 8, 2001    (FR) .................... 01 07559

(51) Int. Cl.
*C12P 13/00* (2006.01)
*C12N 15/00* (2006.01)
*A61K 38/43* (2006.01)
*A61K 38/00* (2006.01)

(52) U.S. Cl. .................... 514/2; 424/94.1; 435/69.1; 435/440

(58) Field of Classification Search .................... 514/2; 424/94.1; 435/69.1, 440
See application file for complete search history.

(56) References Cited

U.S. PATENT DOCUMENTS 6,352,839 B1 * 3/2002 Blanc et al. .................... 435/41
6,833,382 B2 * 12/2004 Blanc et al. .................. 514/410

FOREIGN PATENT DOCUMENTS

| JP | 6038781 A | 2/1994 |
|---|---|---|
| JP | 6062880 A | 3/1994 |
| JP | 10127280 A | 5/1998 |
| WO | WO 95 10604 A | 4/1995 |
| WO | WO 96 01901 A | 1/1996 |
| WO | WO 96 35775 A | 11/1996 |
| WO | WO 98 54308 A | 12/1998 |
| WO | WO 99 07873 A | 2/1999 |
| WO | WO 00 20601 A | 4/2000 |
| WO | WO 00 23609 A | 4/2000 |

OTHER PUBLICATIONS

N. Sans, et al. Eur. J. Biochem. (1988) 173, pp. 123-130.*
A.J. Aspen and A. Meister. Biochemistry (1962) 1(4), pp. 606-612.*

Sans et al., "*Ornithine Cyclodeaminase from Ti Plasmid C58. DNA Sequence, Enzyme Properties, and Regulation of Activity by Arginine*," European Journal of Biochemistry, vol. 173, No. 1, 1988, pp. 123-130.

Schindler, U. et al., "*Ornithine Cyclodeaminase from Octopine Ti Plasmid Arch5. Identification, DNA Sequence, Enzyme Properties and Comparison with Gene and Enzyme of Nopaline Ti Plasmid C58*," Journal of Bacteriology, vol. 171, No. 2, 1989, pp. 847-854.

Makrides, "*Strategies for Achieving High-Level Expression of Genes in Escherichia coli*," Microbiological Reviews, American Society for Microbiology, Washington, DC, vol. 60, n.3, Sep. 1, 1996, pp. 512-538.

Williams, D. et al., "*Design, Synthesis and Expression of a Human Interleukin-2 Gene Incorporating the Codon Usage Bias Found in Highly Expressed Escherichi coli genes*," Nucleic Acids Research, vol. 16, No. 22, pp. 10453-10467.

Stanlon, V. et al., "*Catabolism of Arginine Citrulline and Ornithine by Pseudomonas and Related Bacteria*," Journal of General Microbiology, vol. 133, No. 9, 1987, pp. 2487-2496.

Costilow, R. et al., "*Ornithine Cyclase (deaminating). Purification of a Protein that Converts Ornithine to Proline and Definitions of the Optimal Assay Conditions*," Journal of Biological Chemistry, vol. 246, No. 21, 1971, pp. 6665-6660.

Wickwire, B. et al., "*Pipecolic Acid Biosynthesis in Rhizoctonia Leguminicola. 1. The Lysine, Saccharopine delta-1-piperideine-6-carboxylic Acid Pathway*," Journal of Biological Chemistry, vol. 265, n.25, pp. 14742-14747, 1990.

Khaw Le et al., "*Mutational Biosynthesis of Novel Rapamycins by a Strain of Streptomyces hygroscopicus NRRL 5491 Disrupted in rapL, encoding a Putative Lysine Cyclodeaminase*," Journal of Bacteriology, vol. 180, No. 4, Feb. 1, 1998, pp. 809-814.

(Continued)

*Primary Examiner*—Samuel W. Liu
(74) *Attorney, Agent, or Firm*—Buchanan, Ingersol & Rooney, PC

(57) ABSTRACT

The invention concerns a method for producing a cyclic L-amino acid of formula (I), characterised in that it consists in reacting a L-diamino acid of formula (II) or an enantiomeric mixture comprising such a L-diamino acid and a corresponding D-diamino acid in variable proportions, in the presence of an ornithine cyclodeaminase or a polypeptide homologous to the ornithine cyclodeaminase.

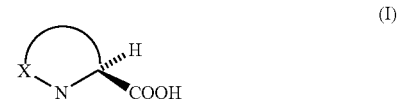

(I)

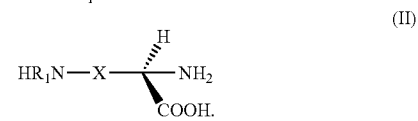

(II)

10 Claims, No Drawings

OTHER PUBLICATIONS

Molnar, I. et al., "*Organisation of the Biosynthetic Gene Cluster for Rapamycin in Streptomyces hygroscopicus: Analysis of Genes Flanking the Polyketide Synthase,*" Gene, vol. 169, No. 1, Feb. 22, 1996, pp. 1-7.

Wu, K. et al., "*The FK520 Gene Cluster of Streptomyces hygroscopicus var. Ascomyceticus (ATCC 19891) Contains Genes for Biosynthesis of Unusual Polyketide Extender Units,*" Gene, vol. 251, No. 1, Jun. 2000, pp. 81-90.

Byrne, K.M. et al., "*The Biosynthesis and Enzymology of an Immunosupressant, Immunomycin, Produced by Streptomyces hygroscopicus var. Ascomyceticus,*" Developments in Industrial Microbiology, vol. 32, 1993, pp. 29-47.

* cited by examiner

STEREOSELECTIVE PREPARATION OF CYCLIC L-AMINO ACIDS

This application is a 371 of PCT/FR02/1983 filed Jun. 10, 2002.

The present invention relates to the stereoselective preparation of cyclic L-amino acids or salts and derivatives thereof.

There is an increasing demand for cyclic amino acids, particularly L-proline, L-pipecolic acid or L-piperazine-2-carboxylic acid and salts thereof because of their use for the synthesis of new medicaments. Given that these are chiral molecules, synthesis thereof is difficult.

From the biosynthetic point of view, only the formation of the ring of L-proline has been explained and described. It can be done in two ways:

either by cyclisation of glutamic semialdehyde acid to form Δ1-pyrroline-5-carboxylic acid, followed by a reduction of the unsaturated ring;

or directly from L-ornithine by cyclodeamination.

However, these processes do not provide a satisfactory solution for the synthesis of chiral cyclic amino acids on an industrial scale.

Moreover, an enzymatic activity of direct conversion of L-ornithine into L-proline has been described for the first time in *Clostridium* (R. N. Costilow et al., *J. Biol. Chem.*, 246 (21), (1971), 6655-60; W. L. Muth et al., *J. Biol. Chem.*, 249 (23), (1974), 7457-62, and a total conversion of 20 mM of L-ornithine into L-proline has been obtained in vitro in the presence of the partially purified enzyme. This ornithine cyclodeaminase (ocd) of *Clostridium* has the particular characteristic of being activated by nicotinamide adenine dinucleotide (AND), a cofactor usually involved in the oxidation reactions, and seems to be quite instable when in a purified form. It does not react on D-ornithine, but is inhibited in the presence of 40 mM of D-ornithine, whilst in the presence of 40 mM of L-lysine its activity is not reduced. The possibility that the cyclodeaminase might act on the L-lysine has therefore not even been envisaged by these authors, probably because it is very often acknowledged that the enzymes of the metabolism are very specific.

Some years later, the correlation between the expression of a gene of *Agrobacterium* involved in the degradation of nopaline and an ocd activity was established (N. Sans et al., *Eur. J. Biochem.*, 173 (1988), 123-130), and the gene coding for ocd was then sequenced.

A second very homologous gene was then found in another strain of *Agrobacterium* by the same authors (U. Schindler et al., *J. Bacteriol.*, 171, (1989), 847-854). The properties of the two cyclodeaminases were studied and only an activity on L-ornithine was demonstrated. Thus, again, the possibility that L-lysine might be a substrate of the cyclodeaminase was not envisaged, only its inhibiting effect was examined (Schindler et al., ibid).

Since then the total or partial sequencing of numerous organisms has permitted the identification of several new genes having a strong homology with this ocd gene of *Agrobacterium*. However, neither the enzymatic activity of the polypeptide encoded by each of these genes, nor its spectrum of activity have been studied, this enzyme being considered specific to ornithine. In particular, the specificity of these enzymes and their level of catalytic activity remain unknown even though these are determinant elements for the productivity of an enzymatic process.

For three of these genes found in *Streptomyces*, producers of metabolites derived from L-pipecolic acid, a lysine cyclodeaminase activity for the encoded polypeptide has been postulated (WO-A1-96/01901; L. E. Khaw et al., *J. Bacteriol.*, 180, (1998), 809-814; I. Molnar et al., *Gene,* 169, (1996), 1-7; H. Motamedi et al., *Eur. J. Biochem.*, 249, (1998), 528-534).

Thus it has been suggested that a cyclodeaminase encoded by the gene rapL (Khaw et al., ibid.) or pipA (WO-A-96/01901) could be involved in the synthesis route of Rapamycin via transformation of lysine into pipecolic acid. To date, however, even if it has sometimes been suggested obiter dictum, no activity of cyclodeamination of L-lysine into L-pipecolic acid has been demonstrated, exemplified or quantified. This lack of knowledge of the reaction actually catalysed by these genes is demonstrated by the diversity of hypotheses concerning the biological route leading to pipecolic acid by certain of these authors who also relate in these publications that the conversion of lysine into pipecolic acid could be effected via D-lysine (Khaw et al., ibid.).

Other biochemical studies have described the formation of L-pipecolic acid from α-aminoadipic acid by reduction of an unsaturated ring (A. J. Aspen et al., *Biochemistry*, 1, (4), (1962), 606-612) in *Aspergillus* and, on the basis of isotopic marking experiments, such biosynthesis routes had also been proposed in a *Streptomyces* by persons skilled in the art (J. W. Reed et al., *J. Org. Chem.*, 54 (5), (1989), 1161-65).

The fact that the enzymes of biosynthesis of L-proline, and in particular ornithine cyclodeaminase, had not been proposed for the production of new cyclic amino acids constitutes additional proof that, in the general opinion of persons skilled in the art, it was not possible to achieve the biosynthesis of pipecolic acid in this manner. Thus several biotechnological processes of bioconversion leading to enantiomerically pure forms, and more particularly to the L form of pipecolic acid or of piperazine-2-carboxylic acid, have been protected by patents for several years. The examples appearing in these publications report a maximum production of 15 g/L of the cyclic amino acid; no mention has been found of the use of a cyclodeaminase.

All of these documents, with the exception of only one, describe the resolution of a racemic substrate. They use activities of the N-acylase type (WO 95/10604, WO 99/07873), the amidase type (EP-A-0 686 698), the amino acid oxidase type (JP 06030789), the nitrilase type (JP 06038781, JP 11127885) or the esterase type (WO 00/12745) acting on suitable substrates.

All of these methods have a certain number of drawbacks, amongst which mention may be made of a limitation of the maximum yield to 50% on the racemic mixture, the necessity of a separation of the product thus formed and of the substrate which is not transformable by the enzyme in order to recover the enantiomeric form sought, and the necessity of possible development of recycling of the other enantiomeric form. Only JP 06030781 describes the conversion of L-lysine, a chiral substrate which is commercially available and not very expensive, into L-pipecolic acid by various non-recombinant bacterial isolates, but without the sequence of chemical reactions borrowed in order to effect this bioconversion. The performances, in terms of yield and productivity, mentioned in this document—namely a production in 7 days of approximately 4.2 g/L of L-pipecolic acid from 10 g/L of L-lysine—remain quite insufficient for such a method to be advantageous and economically competitive. One of the objects of the invention is to obtain better performances than that known for the prior art, and in particular production of cyclic amino acids of the order of 5, 10 or even 20 times greater or more than those disclosed in the prior art.

The present applicant has now shown that it is possible to convert with high yields concentrated solutions of diamino acids into solutions of α-imino-cyclic acids, particularly in aqueous solution of ammonium salts of α-imino-cyclic acids, by employing an enzyme encoded by the gene of ornithine cyclodeaminase (EC 4.3.1.12) of the strain of *Agrobacterium* C58 or by a gene homologous thereto, or recombinant microorganisms overproducing such enzymes.

The invention relates to a method of production of a cyclic L-amino acid of formula (I) or of a salt or derivative of an amino acid of formula (I):

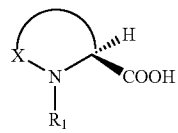

(I)

in which:
* $R_1$ is chosen from amongst the hydrogen atom, a linear or branched alkyl radical having from 1 to 6 carbon atoms and a linear or branched acyl radical having from 1 to 6 carbon atoms; and
* X represents a saturated, or partially or totally unsaturated, linear or branched $C_1$-$C_9$, preferably $C_2$-$C_4$, hydrocarbon chain, optionally comprising in the chain and/or at the end of the chain one or several heteroatoms or heterogroups chosen from amongst O, S, P, $NR_2$, $R_2$ representing H or a $C_1$-$C_4$ alkyl or acyl group, the said chain also being optionally substituted by one or several identical or different radicals chosen from amongst —R, —OR, —SR, =O, —C(O)OR, —C(S)OR, —C(O)NR'R", —C(S)NR'R", —CN, —$NO_2$, —X, —MgX, —NR'R", —NR'C(O)R, —SiR and —SiOR, R, R' and R", identical or different, representing hydrogen or a linear or branched, saturated, or totally or partially unsaturated, hydrocarbon radical having from 2 to 20 carbon atoms, it being understood that R' and R" can form a ring with the atom carrying them, characterised in that:
a) a L-diamino acid of formula (II):

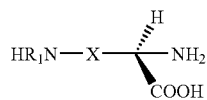

(II)

in which X and $R_1$ are as defined above;
or a salt or derivative thereof,
or an enantiomeric mixture comprising a L-diamino acid of formula (II) and a corresponding D-diamino acid, the salts or derivatives thereof in variable proportions, preferably in an aqueous medium,
is made to react in the presence of an ornithine cyclodeaminase, or a polypeptide homologous to ornithine cyclodeaminase, the enzyme or the homologous polypeptide being obtained from a recombinant expression vector expressing the said enzyme or the said homologous polypeptide,
b) the cyclic L-amino acid of formula (I) or a salt or derivative thereof is recovered in an enantiomeric excess of at least 80%.

"Amino acid derivative of formula (I) or (II)" is understood to mean an amide or ester thereof.

More specifically, the present invention relates to a method of production of a cyclic L-amino acid of formula (I) or a salt or derivative of an amino acid of formula (I):

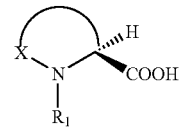

(I)

in which $R_1$ represents H or a $C_1$-$C_6$ alkyl group or a $C_1$-$C_6$ acyl group, and X represents a saturated linear or branched $C_2$-$C_9$, preferably $C_2$-$C_4$, hydrocarbon chain, optionally interrupted by one or several heteroatoms or heterogroups chosen from amongst O, S, $NR_2$, $R_2$ representing H or a $C_1$-$C_4$ alkyl or acyl group, and/or optionally substituted by one or several hydroxy, amino or halogenated groups, characterised in that:
a) a L-diamino acid of formula (II):

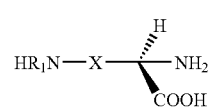

(II)

in which X and $R_1$ are as defined above;
or a salt or derivative thereof,
or an enantiomeric mixture comprising a L-diamino acid of formula (II) and a corresponding D-diamino acid, the salts or derivatives thereof in variable proportions, preferably in an aqueous medium,
is made to react in the presence of an ornithine cyclodeaminase, or a polypeptide homologous to ornithine cyclodeaminase, the enzyme or the homologous polypeptide being obtained from a recombinant expression vector expressing the said enzyme or the said homologous polypeptide, and
b) the cyclic L-amino acid of formula (I) or a salt or derivative thereof is recovered in an enantiomeric excess of at least 80%.

When the hydrocarbon chain has one or several unsaturations of an ethylenic and/or acetylenic nature, these are preferably not carried by the carbon atoms situated in the α position of the nitrogen atoms forming the amine functions of the diamino acid of formula (II).

It is also preferred that, when the hydrocarbon chain has one or several heteroatoms, the said heteroatoms are separated by at least two carbon atoms.

The compounds of formula (I) obtained using the method according to the present invention most often include a ring of 3, 4, 5, 6 or 7 bonds, which are the rings most frequently encountered in the field of organic chemistry. The compounds of formula (I) for which the ring has 5, 6, or 7 bonds are preferred and are the ones which seem the most accessible to the person skilled in the art. However, the method according to the present invention should not be limited to the synthesis of these compounds with rings of 5, 6 or 7 bonds.

The method is also preferred in which the compound of formula (I) comprises a ring of six bonds, X representing a hydrocarbon chain with four bonds. Even more specifically, the method is implemented in order to obtain a compound of formula (I) in which X is a linear or branched alkylene chain. In the present invention, a hydrocarbon chain should be, understood to mean a chain having atoms of carbon and of hydrogen.

For the method according to the present invention, it should be understood that the L-diamino acid of formula (II), as defined above, is placed in the presence of at least one enzyme and/or at least one polypeptide homologous to ornithine cyclodeaminase, obtained from a recombinant expression vector expressing this or these enzyme(s) or homologous polypeptide(s).

Ornithine cyclodeaminase is understood to mean any enzyme capable of cyclising a diamino acid, more precisely an amino-α-amino acid and particularly ornithine and lysine. The ornithine cyclodeaminase to which reference is made in the rest of the text is preferably the ornithine cyclodeaminase (EC 4.3.1.12) of the strain of *Agrobacterium* C58.

The ornithine cyclodeaminase of the strain of *Agrobacterium* C58, coded by a gene carried by the plasmid TiC58, is described by N. Sans et al., *Eur. J. Biochem.*, 173, (1988), 123-130, and its polypeptide sequence is equally accessible on Genbank (gi: 68365).

"Polypeptide homologous to ornithine cyclodeaminase" is understood to mean the polypeptides having a sequence of amino acids homologous to that of an ornithine cyclodeaminase, particularly that of the strain of *Agrobacterium* C58.

These homologous sequences can be defined as the sequences similar to at least 25% of the sequence of amino acids of the ocd gene of *Agrobacterium* and having an ornithine cyclodeaminase activity such as is described by R. N. Costilow et al., *J. Biol. Chem.*, 246, 21, (1971), 6655-60.

The term "similar" refers to the perfect resemblance or identity between the amino acids compared but also to the imperfect resemblance which is termed similarity. This search for similarities in a polypeptide sequence takes into account the conservative substitutions which are substitutions of amino acids of the same class, such as substitutions of amino acids with uncharged side chains (such as asparagine, glutamine, serine, threonine and tyrosine), amino acids with basic side chains (such as lysine, arginine and histidine), amino acids with acidic side chains (such as aspartic acid and glutamic acid), amino acids with apolar side chains (such as glycine, alanine, valine, leucine, isoleucine, proline, phenylalanine, methionine, tryptophan and cysteine).

More generally, "homologous sequence of amino acids" is therefore understood to mean any sequence of amino acids which differs from the sequence of amino acids of ornithine cyclodeaminase coded by the ocd gene of *Agrobacterium* by substitution, deletion and/or insertion of an amino acid or a reduced number of amino acids, particularly by substitution of natural amino acids by non-natural amino acids or amino pseudoacids at positions such that these modifications do not significantly undermine the biological activity of the coded polypeptide.

Advantageously such a homologous sequence of amino acids is similar to at least 35% of the sequence of the polypeptide coded by the ocd gene of *Agrobacterium*, preferably at least 45%.

The homology is usually determined using a sequence analysis software package (for example, Sequence Analysis Software Package of the Genetics Computer Group, University of Wisconsin Biotechnology Center, 1710 University Avenue, Madison, Wis. 53705, USA). Similar sequences of amino acids are aligned in order to obtain the maximum degree of homology (i.e. identity or similarity, as defined above). For this purpose it may be necessary to introduce gaps into the sequence in an artificial manner. Once the optimum alignment is achieved, the degree of homology is established by recording all the positions for which the amino acids of the two sequences compared are identical, relative to the total number of positions.

These polypeptides have the feature in common that they have a α-δ or α-ε diamino deaminase acid activity, without this necessarily having been established hitherto.

Included amongst such homologous sequences are the sequences of polypeptides homologous to ornithine cyclodeaminase of *Agrobacterium* found in the microorganisms belonging to the genera *Agrobacterium*, *Aeropyrum*, *Archaeoglobus*, *Brucella*, *Corynebacterium*, *Halobacterium*, *Mesorhizobium*, *Methanobacterium*, *Pseudomonas*, *Rhizobium*, *Rhodobacter*, *Sinorhizobium*, *Schizosaccharomyces*, *Sulfolobus*, *Thermoplasma*, *Staphylococcus* and *Streptomyces*.

Mention may be made in particular of the sequences of polypeptides homologous to ornithine cyclodeaminase of *Agrobacterium* found in the species or strains listed in Table 1 below:

TABLE 1

Microorganisms having sequences of polypeptides homologous to that of ornithine cyclodeaminase of *Agrobacterium*

| Strain or species | Genbank number (gi:) of the homologous peptide |
|---|---|
| *Aeropyrum pernix* (strain K1) | 7521229 |
| *Agrobacterium tumefaciens* | 1066073 |
| *Agrobacterium tumefaciens* plasmid pAtK84b | 11269716 (fragment) |
| *Agrobacterium tumefaciens* plasmide pTiAch5 | 2498689 |
| *Agrobacterium tumefaciens* plasmide pTiC58 | 68365 |
| *Archaeoglobus fulgidus* | 11499255 |
| *Brucella melitensis* biovar *Abortus* | 1354828 |
| *Corynebacterium glutamicum* | 4127671 |
| *Halobacterium* sp. NRC-1 | 10581639 (ocd1); 10580873 (ocd2) |
| *Mesorhizobium loti* | 13472795 |
| *Mesorhizobium loti* | 13472097 |
| *Mesorhizobium loti* | 13475945 |
| *Mesorhizobium loti*, | 13475655 |
| *Mesorhizobium loti* | 13471680 |
| *Methanobacterium thermoautotrophicum* (strain Delta H), or *Methanothermobacter thermautotrophicus* | 7482770 |
| *Pseudomonas aeruginosa* (strain PAO1) | 11350019 (ocd1); 11350319 (ocd2) |
| Y4tK *Rhizobium* sp. NGR234 | 2182641 |
| *Rhizobium* or *Sinorhizobium meliloti* | 420888 |
| *Rhodobacter capsulatus* | 7437141 |
| *Schizosaccharomyces pombe* | 12044475 |
| *Staphylococcus aureus* | 13700033 |
| *Streptomyces hygroscopicus* | 7481884 |
| *Streptomyces hygroscopicus* var *ascomycetus* | 9280393 |
| *Sulfolobus solfataricus* | 13813523 (ocd1); 13816686 (ocd2) |
| *Thermoplasma acidophilum*, | 10639650 |
| *Thermoplasma volcanium*, | 13541655 |

Mention may also be made of the polypeptide encoded by the gene pipA of *Streptomyces pristinaespiralis* (ATCC-25486) of which the sequence is described in WO-A1-96/01901 and the sequences of polypeptides homologous to the ornithine cyclodeaminase of *Agrobacterium* which may be found in the species or strains producing rapamycin, ascomycin and FK-506, as well as the *Streptomyces* or other microorganisms producing streptogramins, in particular *Streptomyces ioïdensis* (ATCC-11415), *Streptomyces mitakaensis*

(ATCC-15297), *Streptomyces olivaceus* (ATCC-12019), *Streptomyces ostreogriseus* (ATCC-27455), *Streptomyces virginiae* (ATCC-13161).

Mention may also be made of the polypeptides homologous to the ornithine cyclodeaminase of *Agrobacterium* found in eukaryotic organisms such as *Arabidopsis thaliana, Drosophila melanogaster, Homo sapiens, Macropus fuliginosus, Mus musculus*, and *Rattus norvegicus* and listed in the following Table 2:

TABLE 2

Higher organisms having sequences
of polypeptides homologous to that of
the ornithine cyclodeaminase of *Agrobacterium*

| Strain or species | Genbank number (gi:) of the homologous peptide |
|---|---|
| *Arabidopsis thaliana*, | 9950040 |
| *Drosophila melanogaster*, | 7293295 |
| *Homo sapiens*, | 13647115 |
| *Macropus fuliginosus*, | 283930 |
| *Mus musculus*, | 3913376 |
| *Rattus norvegicus* | 5931745 |

In a particular embodiment of the invention, these polypeptides are encoded by genes homologous to that of the ornithine cyclodeaminase of the strain of *Agrobacterium* C58.

"Gene homologous to that of the ornithine cyclodeaminase of the strain of *Agrobacterium* C58" is understood to mean any gene having:

a) a nucleotide sequence similar to the coding sequence of the gene of the ornithine cyclodeaminase of the strain of *Agrobacterium* C58; or b) a nucleotide sequence hybridising with the coding sequence of the gene of the ornithine cyclodeaminase of the strain of *Agrobacterium* C58 or its complementary sequence, under stringent hybridisation conditions; or c) a nucleotide sequence coding for a polypeptide homologous to the ornithine cyclodeaminase of *Agrobacterium* as defined above or having an ornithine cyclodeaminase activity.

Preferably, such a homologous nucleotide sequence according to the invention is similar to at least 75% of the sequence of the ocd gene of *Agrobacterium* or of the gene pipA, rapL, pipA* of sequence SEQ ID No. 1, rapL* of sequence SEQ ID No. 2 and rapL*L* of sequence SEQ ID No. 5 defined below, more preferably at least 85%, or at least 90%.

In a preferred manner, such a homologous nucleotide sequence hybridises specifically to the complementary sequence of the sequence of the ocd gene of *Agrobacterium* or of the gene pipA, rapL, pipA* of sequence SEQ ID No. 1, rapL* of sequence SEQ ID No. 2 and rapL*L* of sequence SEQ ID No. 5 defined below, under stringent conditions. The parameters defining the conditions of stringency depend upon the temperature at which 50% of the matched strands separate (Tm).

For the sequences comprising more than 30 bases, Tm is defined by the relation: Tm=81.5+0.41 (% G+C)+16.6 Log (concentration of cations)−0.63 (% formamide)−(600/number of bases) (Sambrook et al., 1989).

Under appropriately stringent conditions, at which the non-specific sequences do not hybridise, the hybridisation temperature can preferably be from 5 to 10° C. below Tm, and the hybridisation buffers used are preferably solutions with a high ionic strength such as a solution of 6×SSC for example.

The term "similar sequences" used above refers to the perfect resemblance or identity between the nucleotides compared but also to the perfect resemblance which is termed similarity. This search for similarities in the nucleic sequences distinguishes the purines and the pyrimidines for example.

A homologous nucleotide sequence therefore includes any nucleotide sequence which differs from one of the identified sequences by mutation, insertion, deletion or substitution of one or several bases, or by the degeneracy of the genetic code.

Such homologous sequences may be obtained from microorganisms belonging to the genera *Agrobacterium, Aeropyrum, Archaeoglobus, Brucella, Corynebacterium, Halobacterium, Mesorhizobium, Methanobacterium, Pseudomonas, Rhizobium, Rhodobacter, Sinorhizobium, Schizosaccharomyces, Sulfolobus, Thermoplasma, Staphylococcus* and *Streptomyces*.

Mention may be made in particular of the sequences of genes coding for polypeptides homologous to the ornithine cyclodeaminase of *Agrobacterium* found in the species or strains listed in Table 1 above.

Mention may also be made of the sequence of the gene pipA of *Streptomyces pristinaespiralis* (ATCC-25486) described in WO-A1-96/01901 and the sequences of the genes coding for polypeptides homologous to the ornithine cyclodeaminase of *Agrobacterium* which may be found in the species or strains producing rapamycin, ascomycin and FK-506, as well as the *Streptomyces* or other microorganisms producing streptogramins, in particular *Streptomyces ioïdensis* (ATCC-11415), *Streptomyces mitakaensis* (ATCC-15297), *Streptomyces olivaceus* (ATCC-12019), *Streptomyces ostreogriseus* (ATCC-27455), *Streptomyces virginiae* (ATCC-13161).

Mention may also be made of the sequences of eukaryotic genes of *Arabidopsis thaliana, Drosophila melanogaster, Homo sapiens, Macropus fuliginosus, Mus musculus*, and *Rattus norvegicus* which are described as encoding polypeptides homologous to the ornithine cyclodeaminase of *Agrobacterium* and listed in the preceding Table 2.

Amongst the genes which are very suitable for the method according to the invention, mention may be made in particular of the genes rapL of *Streptomyces hygroscopicus* and pipA of *Streptomyces pristinaespirales* of which the sequence is described respectively by Schwecke et al., *Proc. Natl. Acad. Sci.* U.S.A., 92 (17), (1995), 7839-43 and in WO-A1-96/01901. According to an embodiment of the invention, the compound of general formula (II) or the enantiomeric mixture comprising an L-amino acid of formula (II) and a corresponding D-amino acid, salts or derivatives thereof in variable proportions, is placed in the presence of a suspension of the microorganism producing the polypeptide homologous to the ornithine cyclodeaminase.

Preferred homologous genes as described above are synthetic genes obtained by directed mutagenesis as described below.

According to an embodiment of the invention, the compound of formula (II) or the enantiomeric mixture comprising an L-amino acid of formula (II) and a corresponding D-amino acid, salts or derivatives thereof in variable proportions is placed in the presence of an enzyme isolated from the producing microorganism.

According to another embodiment of the invention, the compound of formula (II) or the enantiomeric mixture comprising an L-diamino acid of formula (II) and a corresponding D-diamino acid in variable proportions is placed in the presence of an enzyme in the purified state.

According to another embodiment of the invention, the compound of formula (II) or the enantiomeric mixture comprising an L-diamino acid of formula (II) and a corresponding D-diamino acid in variable proportions is placed in the presence of a recombinant enzyme, this latter embodiment being preferred.

It was found surprisingly that under the conditions of the invention the polypeptides as described above permitted the stereospecific synthesis of the compounds of formula (I) of the invention without necessitating the exogenous addition of AND to the reaction medium.

In an embodiment of the invention, the enzymatic preparation or the cellular suspension which is optionally permeabilised has added to it a compound of formula (II) or a mixture of enantiomers of the compound of formula (II) and of a corresponding D-diamino acid in a concentration greater than approximately 0.05 M, preferably greater than approximately 0.01 M, this same concentration being less than approximately 3 M, and preferably less than 2.5 M, the salts or derivatives thereof, and this is left to incubate at a temperature of between 10° C. and 100° C., advantageously between 20° C. and 70° C., preferably between 25° C. and 45° C. for a period of between several hours and several days, with stirring.

In this way it is possible to obtain molar yields of the compound of formula (I) of at least 20%, advantageously at least 80%, preferably at least 90% with an enantiomeric excess greater than 80%, advantageously greater than 90%, preferably greater than 95%.

Advantageously, the compound of formula (I) is in the form of an ammonium salt.

As a variant, the enzymes extracted from the culture medium or purified with the compound of formula (II) or a mixture of enantiomers of the compound of formula (II) or of a corresponding D-diamino acid may also be put to incubate in a medium which may or may not be buffered at a pH of between 6 and 11 and preferably between 7 and 10.

The product obtained can be collected by precipitation, crystallisation or ion exchange chromatography.

Amongst the substrates preferred for the preparation of a compound of formula (I), mention may be made in particular of L-lysine or a mixture of L- and D-lysine, L-thialysine (S-2-aminoethyl-L-cysteine), L-ornithine, a mixture of L- and D-5-(R,S)-hydroxylysine, a mixture of L- and D-azalysine (γ-N-2-aminoethyldiaminopropionic acid).

In order to render the method more particularly efficient, the overproduction of the polypeptide with ornithine cyclodeaminase activity is particularly advantageous.

With a view to this, the gene of interest coding for a polypeptide as defined above is introduced into a host microorganism, preferably overexpressing the polypeptide.

To this end a vector containing a nucleic acid comprising one of the nucleotide sequences as defined above or a homologous sequence is transferred into a host cell which is cultured under conditions permitting the expression, preferably the overexpression, of the corresponding polypeptide.

The nucleic acid sequence of interest can be inserted into an expression vector in which it is linked in an operative manner to elements permitting the regulation of the expression thereof, such as in particular promoters, activators and/or terminators of transcription.

The signals controlling the expression of the nucleotide sequences (amongst which mention may be made of the promoters, the activators and the sequences of termination) are chosen as a function of the host cell used. For this purpose the nucleotide sequences according to the invention can be inserted into vectors with autonomous replication within the chosen host, or vectors which integrate into the chosen host. Such vectors will be prepared according to the methods currently used by the person skilled in the art, and the clones resulting therefrom can be introduced into an appropriate host by standard methods.

Amongst the preferred vectors, mention may be made of the plasmids pTZ18 (Sigma, St-Louis), pQE70 (Qiagen, Munich) and PQE60 (Qiagen, Munich).

When they were used, the QIAGEN plasmids showed the major drawback of involving the formation of polyhistidines in the enzymes obtained. Therefore, these plasmids have to be modified in order to overcome this drawback. Thus the coding sequences must be modified or disrupted. These modifications did not bring about any difference in terms of level of expression of the gene encoding cyclodeaminase.

The expression vectors are introduced into the host cells and these latter are cultured under conditions permitting the replication and/or the expression of the transfected nucleotide sequence.

Examples of host cells include in particular E. coli, preferably the strains Escherichia coli DH5α, Escherichia coli β2033, and Escherichia coli K12 (MG1655). However, other host organisms belonging to different genera are equally suitable.

Particularly interesting results are obtained when E coli is transfected with genes modified relative to the corresponding native genes in such a way as to permit optimum expression of the gene of interest in E. coli.

The heterologous gene is modified in such a way as to comprise a proportion of less than 65%, advantageously less than 55% of bases G+C, whilst encoding the same polypeptide as the native gene or a homologous polypeptide as defined previously.

Thus for a given amino acid encoded by a codon of native DNA, if need be the third base of the codon is replaced, or the second base of the codon when this is G or C, by A or T, when the codon obtained corresponds to the same amino acid as that encoded by the native codon.

The modified genes which have made it possible to obtain the best rates of expression and equally the highest yields of α-imino-cyclic acids are those in which the native codons have been replaced for a given amino acid of the polypeptide having amino acid cyclodeaminase activity by the following respective codons shown in Table 3.

TABLE 3

| Conversion code used | | |
|---|---|---|
| Amino acid | | Codon used |
| A | Ala | GCA |
| R | Arg | CGT |
| N | Asn | AAT |
| D | Asp | GAT |
| C | Cys | TGT |
| Q | Gln | CAA |
| E | Glu | GAA |
| G | Gly | GGT |
| H | His | CAT |
| I | Ile | ATT |
| L | Leu | TTA |
| K | Lys | AAA |
| M | Met | ATG |
| F | Phe | TTT |
| P | Pro | CCA |
| S | Ser | TCT |
| T | Thr | ACT |
| W | Trp | TGG |
| Y | Tyr | TAT |
| V | Val | GTT |

The modified genes were obtained by assembling sections obtained by PCR and directed mutagenesis from corresponding native genes.

Amongst the modified genes which gave the best results, mention may be made of the modified genes pipA* and rapL** having respectively the sequences SEQ ID No. 1 and SEQ ID No. 5 shown in the annex to the present application.

The polynucleotides corresponding to these modified genes constitute a further subject of the invention.

The gene pipA* was obtained from the sequence of the polypeptide encoded by the gene pipA of *Streptomyces pristinaespiralis* shown in the annex as sequence SEQ ID No. 3.

The gene rapL** was obtained from the sequence of the polypeptide encoded by the gene rapL of *Streptomyces hygroscopicus* shown in the annex as sequence SEQ ID No. 4.

The modified genes are inserted into cloning vectors as described above for the native genes transfected into recombinant hosts.

The host microorganisms which are, as the case may be, recombinant, and include a gene existing in the native state or modified as described above are cultivated, optionally in the presence of an expression inductor, for example IPTG.

When the cells reach a density of the order of at least one unit of absorbance at 600 nm for standard cultures and of the order of several tens or more of such units for high-density cultures, they are separated from their culture medium and subjected to a permeabilisation treatment which may be physical (for example, alternating freezing and thawing treatments, treatments with ultrasound or with a French press, mechanical crushing) or chemical (for example, addition of solvent or complexing agents such as EDTA), or enzymatic (for example, addition of lysozyme).

The cellular suspension can then be used in order to achieve the preparation of the products of formula (II) as described above where the protein of interest which is produced can then be recovered and purified. By way of example, using a method of the "Fed-batch" type or equivalent, concentrations are obtained, expressed in grams of dry cells per litre of cellular suspension, greater than approximately 10 g/L, advantageously greater than 30 g/L. These same concentrations are, as a general rule, less than 60 g/L, or even less than 50 g/L, without this indicating an insuperable limit.

The purification methods used are known to the person skilled in the art. The recombinant polypeptide obtained can be purified on the basis of lysates and cellular extracts, the supernatant of the culture medium, by methods used individually or in combination, such as fractionation, methods of chromatography, techniques of immuno-affinity with the aid of specific mono- or polyclonal antibodies, etc.

However, it is not necessary to recover this protein.

According to an advantageous embodiment, the host cells producing the polypeptide having the enzymatic activity, required are destroyed so that their cytoplasmic content is released into the medium containing the diamino acid substrate of which the two amine groups are distant (by the shortest route when several routes are possible) by four or five bonds, in the L form or in the form of a mixture of enantiomers and in such a way as to enable the enzyme and its substrate to be brought together.

The following examples illustrate the invention.

EXAMPLE 1

Amplification by PCR of the Gene pipA of *Streptomyces pristinaespiralis* from the Total DNA of the Strain 1.1 Extraction of the Total DNA The strain *Streptomyces pristinaespiralis* ATCC 25486 was cultivated at 28° C. for 24 hours in the medium TSB (DIFCO), then 10 mL of the culture thus obtained were centrifuged for 5 minutes at 11000 g. The centrifugation pellet was taken up by 1 mL of a solution of 10 mM Tris pH 8.0 containing 2 mM of EDTA and 5 mg/mL of lysozyme. The suspension thus obtained was left with stirring for 30 minutes at 37° C., then 100 µL of a 20% solution of SDS were added. After incubation at 30° C. for several minutes, 125 µL of a solution of proteinase K at 2 mg/mnL were again added. Then the extraction of the DNA was carried out using the reagents of the kit DNeasy Tissue Kit (QIAGEN, Munich) following the supplier's instructions. The DNA thus extracted was purified by phenol/chloroform extraction, precipitated by ethanol and taken up in 100 µl of water.

1.2 Amplification of the Gene pipA

The gene pipA was amplified by PCR from the total DNA thus prepared using, for the synthesis of the primers, its sequence described in the patent WO-A1-96/01901. The reaction was carried out in a volume of 50 µL of buffer 20 mM Tris-HCl pH 8.8 containing 10 mM KCl, 10 mM $(NH_4)_2SO_4$, 2 mM $MgSO_4$, 0.1% Triton X-100, 2 µL of the total DNA solution, 250 µM of each of the four dNTP, 1 unit of Vent DNA Polymerase (BioLabs) and 500 nM of each of the following two oligodeoxynucleotides:

5' CCCGAATTCCGACACCACGCACGGACGAGAAG (SEQ ID NO: 6)

5' CCCTGCAGGCATCTCTCTCCTCGCGAGGGC (SEQ ID NO: 7).

The PCR procedure applied began by a step of denaturation at 97° C. for 4 minutes followed by incubation at 80° C. for 1 minute, and continued with 5 cycles characterised by a sequence of 1 minute of denaturation at 97° C. followed by 1 minute of hybridisation at 55° C., then 1 minute 30 seconds of elongation at 72° C. Then 40 cycles characterised by a sequence of 1 minute of denaturation at 97° C., followed by 1 minute of hybridisation at 50° C., then 1 minute 30 seconds of elongation at 72° C., were carried out. The procedure was completed by a step of elongation at 72° C. for 10 minutes.

The fragment thus amplified was purified on the column of the Qiaquick PCR purification kit (QIAGEN), then digested by EcoRI and PstI and cloned in the vector pTZ18 (SIGMA, St-Louis, Mo.) previously cut. Two plasmid constructions (pKT 35, pKT 36) obtained following independent PCR amplifications were sequenced. The sequences of these two fragments thus cloned were identical. The specified protein, of sequence SEQ ID No. 3, differs however by an amino acid (alanine) at position 87 relative to the sequence published in WO-A1-96/01901 (glycine).

EXAMPLE 2

Amplification by PCR of the Gene rapL of *Streptomyces hygroscopicus* from a Suspension of Cells of the Strain.

The strain *Streptomyces hygroscopicus* ATCC 29253 was cultivated at 28° C. for 24 hours in the medium TSB (DIFCO). 50 µL of the cellular suspension thus obtained were subjected to the following steps of heating and cooling: 30 seconds at 65° C., 30 seconds at 8° C., 90 seconds at 65° C., 180 seconds at 97° C., 60 seconds at 8° C., 180 seconds at 65° C., 60 seconds at 97° C., 60 seconds at 65° C., 20 minutes at 80° C.

The amplification of the gene rapL was carried out by PCR from a suspension of cells using its described sequence (Schwecke et al., 1995) for the synthesis of the primers. The reaction was carried out in a volume of 50 µL of buffer 20 mM Tris-HCl pH 8.8 containing 10 mM KCl, 10 mM $(NH_4)_2SO_4$, 2 mM $MgSO_4$, 0.1% Triton X-100, 10 µL of the suspension of cells previously treated, 250 µM of each of the four dNTP, 1 unit of Vent DNA Polymerase (BioLabs) and 500 nM of each of the following two oligodeoxynucleotides:

5' CCCGAATTCGAGGTTGCATGCAGACCAAGGTTCTGTGCCAG (SEQ ID NO: 8)

5' CCCAAGCTTAGATCTTTATTACAGCGAGTACGGATCGAGGACG (SEQ ID NO: 9)

The PCR procedure applied began by a step of denaturation at 97° C. for 4 minutes followed by incubation at 80° C. for 1 minute, and continued first of all with 5 cycles characterised by a sequence of 1 minute of denaturation at 97° C., followed by 1 minute of hybridisation at 60° C., then 1 minute 30 seconds of elongation at 72° C., then by 5 new cycles characterised by a sequence of 1 minute of denaturation at is 97° C., followed by 1 minute of hybridisation at 52° C., then 1 minute 30 seconds of elongation at 72° C. Then 30 cycles characterised by a sequence of 1 minute of denaturation at 97° C., followed by 1 minute of hybridisation at 50° C., then 1 minute 30 seconds of elongation at 72° C., were carried out. The procedure was completed by a step of elongation at 72° C. for 10 minutes.

The fragment thus amplified was purified on the column of the Qiaquick PCR. purification kit (QIAGEN), then digested by EcoRI and HindIII and cloned in the vector pTZ18 previously cut. Three plasmid constructions obtained (pKT 30, pKT 31, pKT 34) following independent PCR amplifications were sequenced. The sequences of these three fragments thus cloned were identical. The specified protein, of sequence SEQ ID No. 4, differs however by five amino acids relative to the sequence published by Schwecke et al., that is to say that the protein according to the invention contains in positions 50, 84, 102, 127 and 129 respectively a residue of threonine, glutamine, aspartic acid, alanine and alanine.

EXAMPLE 3

Total Synthesis by PCR of the Gene pipA*

The gene pipA with a size of 1066 bp derived from *Streptomyces pristinaespiralis* and of which the sequence is described in the patent WO-A1-96/01901 is composed of a proportion of G+C of 69.6%. This gene has been rewritten according to the genetic code optimised for the expression in *Escherichia coli* described in Table 3. The rewritten gene pipA* of sequence SEQ ID No. 1 is henceforth composed of a proportion of G+C of 38%. In order to introduce a single restriction site KpnI, the threonine residue 97 was encoded by ACC instead of ACT provided by the code of Table 3. Two codons for termination of the translation TAA were also added in position 15 and 1080 ($1^{st}$ nucleotide of the codon), respectively of the sequence SEQ ID No. 1, and the single restriction sites EcoRI and NcoI on the one hand, HindIII on the other hand, were introduced respectively at 5' and 3' of the gene thus permitting its insertion into a cloning vector.

The synthesis of the gene pipA* was carried out by assembling two sections EcoRI-KpnI (section 1 of 305 bp—nucleotide 1 to nucleotide 304) and KpnI-HindIII (section 2 of 798 bp—nucleotide 305 to nucleotide 1092).

Each section was synthesised by extension of single-strand oligonucleotides of a length of 50 to 60 nucleotides overlapping ("sense" and "antisense" strands), followed by an amplification by end oligonucleotides 5' and 3'.

Synthesis of the section 1: The PCR reaction was carried out in a volume of 100 μL of buffer 20 mM Tris-HCl pH 8.8 containing 10 mM KCl, 10 mM $(NH_4)_2SO_4$, 2 mM $MgSO_4$, 0.1% Triton X-100, 0.01 μM of the oligonucleotides listed below, 0.3 mM of each of the four dNTP and 2 units of Vent DNA Polymerase (BioLabs). The PCR procedure applied was composed of 30 cycles characterised by a sequence of 30 seconds of denaturation at 96° C., followed by 30 seconds of hybridisation at 55° C., then 30 seconds of elongation at 72° C. At cycle number 10, the oligonucleotides of the ends 5' (PIPAUP) and 3' (PIPAD1) were added at a final concentration of 0.5 μM. At the end of cycle 30, a period of elongation of 2 minutes at 72° C. was added.

The following oligonucleotides were used for the reaction: PipaV0, PipaV2, PipaV4, PipaV6, PipaV8, PipaD4, PipaD5, PipaD6 and PipaD7. The sequences of these oligonucleotides are described in Table 4.

The PCR product thus obtained was purified on the column of the Qiaquick PCR purification kit (QIAGEN)) then digested successively by the restriction enzymes KpnI and EcoRI, and again purified on agarose gel. A band of apparent size of 300 bp was extracted from the gel using the Qiaquick gel extraction kit (QIAGEN). This purified PCR product was then ligated to the vector pTZ18, previously digested by the enzymes EcoRI and KpnI and purified on agarose gel, by the T4 DNA ligase (BioLabs). The ligation reaction is carried out overnight at 16° C. in the ligation buffer supplied with the enzyme. The ligation product was then transformed in the strain *E. Coli* DH5α CIP104738 (D. Hanahan, *J. Mol. Biol.*, 166, (1983), 557-580) by thermal shock and selected recombinant clones on agar LB medium (DIFCO) supplemented with ampicillin (100 mg/L).

The plasmids contained in the transformants resistant to ampicillin were isolated using the plasmid preparation system QLAprep Spin Miniprep Kit (QIAGEN). For four of these plasmids, of which the analysis by appropriate restriction enzymes showed an insert of expected size, the fragments EcoRI-KpnI were sequenced. Each of the sequences of the four constructions contained between one and three deviations relative to the expected sequence. The plasmid pSP23 for which the sequence of the fragment was correct with the exception of a deletion of 6 bp was subjected to a step of directed mutagenesis following a published method (Ansaldi et al., *Anal. Biochem.*, 234, (1996), 110-111) to correct this deletion. The plasmid pSP39 was obtained in this way. The sequencing of the fragment EcoRI-KpnI of the plasmid pSP39 was carried out and the sequence obtained was found to conform to the sequence expected.

Synthesis of section 2: The PCR reaction for the synthesis of the section KpnI-HindIII was carried out is described for the section 1 with the exception of the period of elongation, the duration of which was extended to 1 minute for the 30 cycles and to 4 minutes at the end of the procedure. At cycle number 10, the oligonucleotides of the ends 5' (PIPAV29) and 3' (PIPAD3) were added at a final concentration of 0.5 μM.

The following oligonucleotides were used for the reaction PipaV8, PipaV10, PipaV12, PipaV14, PipaV16, PipaV18, PipaV20, PipaV22, PipaV24, PipaV26, PipaV28, PipaD8, Pipab9, PipaD10, PipaD11, PipaD12, PipaD13, PipaD14, PipaD15, PipaD16 and PipaD17. The sequences of these oligonucleotides are described in Table 4.

The PCR product was purified on the column of the Qiaquick PCR purification kit (QIAGEN), then digested by the restriction enzymes KpnI and HindIII and ligated to the vector pTZ18 previously digested by the same enzymes. The transformation of the strain *E. coli* DH5α, and the selection of the transformants and the analysis of the plasmids were carried out as described above for section 1. The plasmid pSP25 for which the sequence of the fragment KpnI-HindIII had five deviations relative to the expected sequence was subjected to several steps of directed mutagenesis (Ansaldi et al., 1996, ibid) to correct these errors. The plasmid pSP42 was obtained in this way.

Assembly of the 2 sections: The entire gene pipA* was assembled by cloning of the fragment KpnI-HindIII extracted from the plasmid pSP42 in the plasmid pSP39 previously cut by the enzymes KpnI and HindIII. One of the resulting plasmids, the plasmid pSP43 containing a fragment EcoRI-HindIII of expected size was sequenced and the sequence of the gene was thus verified.

TABLE 4

Synthesis of the pipA* gene sequence of the oligonucleotides (SEQ ID NOS 10-43 are disclosed respectively in order of appearance)

| Name | Sequence |
| --- | --- |
| Pipa V0 | 5' TTCCAAGGAATTTGTTTACCCAATCTTCAGTCCGTTCGAATTCGAGGTTCC |
| Pipa V2 | 5' TGATGTTGCAGAAGTTGTTGCAGCAGTTGGTCGTGATGAATTAATGCGTC |
| Pipa V4 | 5' CAGAAATTGGTCGTGGTGAACGTCATTTATCTCCATTACGTGGTGGTTTA |
| Pipa V6 | 5' GAATGGATGCCACATCGTGAACCAGGTGATCATATTACTTTAAAAACTGT |
| Pipa V8 | 5' TGGTTTACCAACTATTTTAGGTACCGTTGCACGTTATGATGATACTACTG |
| Pipa D4 | 5' ATA GTT GGT AAA CCA AAA CGA CCT GGA TTT GCT GGA GAA TAA CCA ACA GTT TTT AAA GTA |
| Pipa D5 | 5' ATG TGG CAT CCA TTC CCA AAT ACC TGG AAC TGG TTC AGA ACG TTC TAA ACC ACC ACG TAA 3' |
| Pipa D6 | 5' CAC GAG CAA TTT CTG CTA AAC CAC CAG TTA AAC GAT CGA TAA TAC GAC GCA TTA ATT CAT 3' |
| Pipa D7 | 5' ACT TCT GCA ACA TCA CGA CGA CCT AAA ACC CAA GTT TCC ATG GAA CCT CGA ATT CG 3' |
| External oligos: | |
| PIPA UP | 5' CCCGAATTCGAGGTTCCATGGAAAC |
| PIPA D1 | 5' CAGTAGTATCATCATAACGTGC |
| Fragment KpnI-HindIII: | |
| Pipa V8 | TGGTTTACCAACTATTTTAGGTACCGTTGCACGTTATGATGATACTACTG |
| Pipa V10 | TATTAACTGCATTACGTACTGGTGCAGCATCTGCTGTTGCATCTCGTTTA |
| Pipa V12 | TTAATTGGTACTGGTGCACAAGCAGTTACTCAATTACATGCATTATCTTT |
| Pipa V14 | GGATACTGATCCAGCACATCGTGAATCTTTTGCACGTCGTGCAGCATTTA |
| Pipa V16 | CACGTATTGCAGCAGAAGCAGATGTTATTTCTACTGCAACTTCTGTTGCA |
| Pipa V18 | GGTGTTCGTGAACATTTACATATTAATGCAGTTGGTGCAGATTTAGTTGG |
| Pipa V20 | ACGTGCATTTGTTACTGCAGATCATCCAGAACAAGCATTACGTGAAGGTG |
| Pipa V22 | GTCCACAATTAGCACATTTATGTGCAGATCCAGCAGCAGCAGCAGGTCGT |
| PipaV24 | GGTTTTGCATTTGAAGATGCATTAGCAATGGAAGTTTTTTTAGAAGCAGC |
| Pipa V26 | TATTGAACATCATCCAGGTGATGCATTAGATCCATATGCATTACAACCAT |
| Pipa V28 | 5' ATA AAG ATC TAA GCT TCC CC |
| Pipa D8 | 5' GGGG AAG CTT AGA TCT TTA TTA ATG TGC TGG TGC TGC TAA TGG TAA TGG TAA TGG TTG TAA TGC AT 3' |
| Pipa D9 | 5' GGA TGA TGT TCA ATA CCA ACA CGA ATA CCT AAA TCA CGT TCT GCT GCT GCT TCT AAA AAA 3' |
| Pipa D10 | 5' TTC AAA TGC AAA ACC AGT AGA ATC AAA AAC AGA TAA AGT ATC TTG ACG ACC TGC TGC TGC 3' |
| Pipa D11 | 5' GTG CTA ATT GTG GAC CTA AAC GAT CAG CAG ATA ATT GTT GAC ATT CAC CTT CAC GTA ATG 3' |

TABLE 4-continued

Synthesis of the pipA* gene sequence of the oligonucleotides (SEQ ID NOS 10-43 are disclosed respectively in order of appearance)

| Pipa D12 | 5' GTA ACA AAT GCA CGT TCT AAT AAA CCT AAT GGT AAT TCA GTT TTA CCA ACT AAA TCT GCA 3' |
|---|---|
| Pipa D13 | 5' ATG TTC ACG AAC ACC AGT ATC TGG TAA AAC TGG ACC TTG ACC AAC TGC AAC AGA AGT TGC 3' |
| Pipa D14 | 5' CTG CTG CAA TAC GTG CTG GTT CTG CAA TTT CAA CAG AAA CAC CAG TAA ATG CTG CAC GAC 3' |
| Pipa D15 | 5' GCT GGA TCA GTA TCC CAA ACT AAT GCA CGT TGT AAT GGT AAA ACT AAA GAT AAT GCA TGC 3' |
| Pipa D16 | 5' ACC AGT ACC AAT TAA ACC TAA AGT ATG AGA ATC TGG ACG TGC TAA TAA ACG AGA TGC AAC 3' |
| Pipa D17 | 5' GTA ATG CAG TTA ATA AAA CAC CAT CCA TTA ATG CAG TTA ATG CAC CAG TAG TAT CAT CAT 3' |
| External oligos: | |
| PIPA V29 | 5' CTA TTT TAG GTA CCG TTG CA |
| PIPA D3 | 5' CCCAAGCTTAGATCTTTATTAATGTG |

EXAMPLE 4

Total Synthesis by Ligation of the Gene rapL* and Obtaining the Variant rapL**

The gene rapL of a size of 1029 bp derived from *Streptomyces hygroscopicus* and of which the sequence has been published (Schwecke et al., 1995, ibid) is composed of a proportion of G+C of 68%. This gene has been rewritten according to the genetic code employed for the synthesis of the gene pipA* in Example 3. The rewritten gene rapL* of sequence SEQ ID No. 2 is henceforth composed of a proportion of G+C of 38%. In order to introduce a single restriction site KpnI, the threonine residue 97 was encoded by ACC instead of ACT provided by the code shown in Table 3. Two codons TAA for termination of the translation were also added and single restriction sites EcoRI and SphI on the one hand, HindIII on the other hand were introduced respectively at 5' and 3' of the gene thus permitting its insertion into different cloning vectors.

The total synthesis of the gene rapL* was carried out by assembling the three sections EcoRI-KpnI (section 1 of 305 bp), KpnI-PstI (section 2 of 316 bp), and PstI-HindIII (section 3 of 440 bp).

Each section was synthesised by ligation of phosphorylated single-strand oligonucleotides at 5' of a length of 50 nucleotides on average, covering the totality of the sequence to be cloned ("sense" and "antisense" strands) and overlapping. The sequences and positions of these oligonucleotides are described in Table 5. The oligonucleotides, mixed in equimolar fashion (1 μM) in the overlapping buffer (20 mM Tris-HCl, pH 8; 0.08 M NaCl) in a final volume of 20 μL, were heated for 10 minutes at 70° C. and kept in the heating block until they returned to ambient temperature. The product thus obtained was then ligated by the T4 DNA ligase overnight at 16° C. in the presence of the vector pTZ18 (molar concentration ratio vector/oligonucleotides 1/100) previously digested by the appropriate restriction enzymes.

The ligation product was used to transform by electroporation the strain β2033 (*E. coli* K12, pro, thi, rpsL, hsdS, ΔlacZ, F' (ΔlacZM15, lacI$^q$, traD36, proA+, proB+)) and the recombinant clones were selected on agar LB medium containing 100 μg/mL of ampicillin, 0.5 mM IPTG and 30 μg/mL X-Gal.

The plasmids contained in several white transformants resistant to ampicillin were isolated using the plasmid preparation system QIAprep Spin Miniprep Kit (QIAGEN). For each section, the inserts of two to four plasmids, of which the analysis by appropriate restriction enzymes showed a fragment of the expected size, were sequenced.

Synthesis of the Section 1:

The plasmid pTZ18 cut by EcoRI and KpnI was ligated with the following oligonucleotides (of which the sequence is illustrated in Table 5): IcdV-1, IcdV-2, IcdV-3, IcdV-4, IcdV-5, IcdV-6, IcdVrev-16, IcdVrev-17, IcdVrev-18, IcdVrev-19, IcdVrev-20, IcdVrev-21, IcdVrev-22. The plasmid pSP3, of which the sequence of the insert had only two deviations relative to the expected sequence, was retained. The two errors were corrected by directed mutagenesis according to a published method (Ansaldi et al., 1996, ibid) and the corrections confirmed by sequencing of the insert of the resulting plasmid pSP14.

Synthesis of the Section 2:

The plasmid pTZ18 cut by KpnI and PstI was ligated with the following oligonucleotides (of which the sequence is illustrated in Table 5): IcdV-7, IcdV-8, IcdV-9, IcdV-10, IcdV-11, IcdV-12, IcdVrev-9, IcdVrev-10, IcdVrev-11, IcdVrev-12 IcdVrev-13, IcdVrev-14, IcdVrev-15. The plasmid pSP8, of which the sequence of the insert had only one deviation relative to the expected sequence, was retained. The error was corrected by directed mutagenesis (Ansaldi et al., 1996, ibid) and the correction confirmed by sequencing of the insert of the resulting plasmid pSP15.

Synthesis of the Section 3:

The plasmid pTZ18 cut by PstI and HindIII was ligated with the following oligonucleotides (of which the sequence is illustrated in Table 5): IcdV-13, IcdV-14, IcdV-15, IcdV-16, IcdV-17, IcdV-18, IcdV-19, IcdV-20, IcdV-21, IcdVrev-1, IcdVrev-2, IcdVrev-3, IcdVrev-4, IcdVrev-5, IcdVrev-6, IcdVrev-7, IcdVrev-8. The plasmid pSP12, of which the sequence of the insert had only one deletion of 25 bp and one point deviation, was retained. The two errors were corrected by directed mutagenesis (Ansaldi et al., 1996, ibid) and the corrections confirmed by sequencing of the insert of the resulting plasmid pSP26.

Assembly of the 3 sections: The corrected fragments KpnI-PstI, then PstI-HindIII are sub-cloned successively in the plasmid pSP14 already containing the fragment EcoRI-KpnI, thus reconstituting the synthetic gene rapL*. The sequence of the gene rapL* of the resulting plasmid pSP33 was confirmed by sequencing.

Obtaining the variant rapL (Sequence SEQ ID No. 5): The variant rapL was obtained from the gene rapL* of the plasmid pSP33 by introducing by directed mutagenesis (Ansaldi et al., 1996, ibid) the five changes necessary so that the protein coded by the gene rapL is the same as that coded by the amplified and sequenced gene described in Example 2 and corresponds to the sequence SEQ ID No. 4, whilst adhering to the genetic code described in Table 3. A plasmid pSP36 derived from the plasmid pTZ18 and containing the gene rapL was thus obtained.

TABLE 5

Synthesis of the rapL* sequence of the oligonucleotides (SEQ ID NOS 44-86 are disclosed respectively in order of appearance)

Fragment EcoRI-KpnI:
"Sense" strand:

| | |
|---|---|
| IcdV-1: | 5'-AATTCGAGGTTGCATGCAAACTAAAGTTTTATGTCAACGTGATATTAA-3' |
| IcdV-2: | 5' p-ACGTATTTTATCTGTTGTT GGTCGTGATGTT  ATG ATG GAT CGT  TTA ATT T-3' |
| IcdV-3: | 5' p-CTGAAGTTCAT  GCA GGT TTT GCA CGT TTA GGT CGT  GGT GAAACT  GATGAA-3' |
| IcdV-4: | 5' p-CCACCA  CCA CGT CCA GGT TTT GCA CGT GGT  GGT  GAT GTT  CCAGGT  GTTAT-3' |
| IcdV-5: | 5' p-T GAA TTT ATG CCA CAT CGT GCA TCT GGT ATT  GGT GTTACT  ATGAAA  ACTG-3' |
| IcdV-6: | 5' p-TT TCT TAT TCT CCA GAA AAT TTT GAA CGT TTTAAT TTACCA  ACT ATT GTT GGT AC-3' |

Brin "anti-sens":

| | |
|---|---|
| IcdVrev-16: | 5' p-CAACAATAG TTGGTAAATTAAAA-3' |
| IcdVrev-17: | 5' p-CGTTCAAAATTTTCTGGAGAATAAGAAACAGTTTTCATAGTAACACCAAT-3' |
| IcdVrev-18: | 5' p-ACCAGATGCACGATGTGGCATAAATTCAATAACACCTGGAACATCACCA-3' |
| IcdVrev-19: | 5' p-CCACGTGCAAAACCTGGACGTGGTGGTGGTTCATCAGTTTCACCACGACCT-3' |
| IcdVrev-20: | 5' p-AAACGTGCAAAACCTGCATGAACTTCAGAAATTAAACGATCCATCATAAC-3' |
| IcdVrev-21: | 5' p-ATCACGACCAACAACAGATAAAATACGTTTAATATCACGTTGA-3' |
| IcdVrev-22: | 5' p-CATAAAACTTTAGTTTGCATGCAACCTCG-3' |

Fragment KpnI-PstI:
"Sense" strand:

| | |
|---|---|
| IcdV-7: | 5' p-CGTTTCT  CGT TTA GGT GAT GATTCTT  GGTTCT ATG  GTT GCA TTA GC-3' |
| IcdV-8: | 5' p-A  GAT GCA GCAACTATT ACT GCAATGCGTACT  GGT GCA  GTT GCA TCT GTT A-3' |
| IcdV-9: | 5' p-CT ACT CGT TTATTAGCACGTCCAGGT  TCT ACT ACT TTA  GCA TTA ATT GGT-3' |
| IcdV-10: | 5' p-GCA  GGT GCACAA  GCAGTTACT CAA GCA CAT GCA  TTA TCT CGT GTT TTA CC-3' |
| IcdV-11: | 5' p-A TTA GAACGT  ATTTTA  ATTTCTGAT ATT AAA GCA GAA CAT GCA GAA TCT T-3' |
| IcdV-12: | 5' p-TTGCAGGTCGT  GTT GCA TTTTTAGAA TTA CCA GTT GAA GTT ACT GATGCAGCAACT  GCA ATG GCA ACT GCA-3' |

TABLE 5-continued

Synthesis of the rapL* sequence of the oligonucleotides (SEQ ID NOS 44-86 are disclosed respectively in order of appearance)

"Antisense" strand:

IcdVrev-9:     5' p-GTTGCCATTGCAGTTGCTGCATCAGTAACTTCAA-3'

IcdVrev-10:    5' p-CTGGTAATTCTAAAAATGCAACACGACCTGCAAAAGATTCTGCATGTTCTGCTTT-3'

IcdVrev-11:    5' p-AATATCAGAAATTAAAATACGTTCTAATGGTAAAACACGAGATAATGCA-3'

IcdVrev-12:    5' p-TGTGCTTGAGTAACTGCTTGTGCACCTGCACCAATTAATGCTAAAGTAGTA-3'

IcdVrev-13:    5' p-GAACCTGGACGTGCTAATAAACGAGTAGTAACAGATGCAACTGCACCAGT-3'

IcdVrev-14:    5' p-ACGCATTGCAGTAATAGTTGCTGCATCTGCTAATGCAACC-3'

IcdVrev-15:    5' p-ATAGAACCAGAATCATCACCTAAACGAGAAACGGTAC-3'

Fragment PstI-HindIII:
"Sense" strand:

IcdV-13:       5' p-GATGTTTTA  TGT ACT GTT ACTTCTGTTCC -3'

IcdV-14:       5' p-A GTT GGT GGT GGT CCAGTTGTTCCA  GCA  GAA CCA  CGTCAAGCACAT  TTA C-3'

IcdV-15:       5' p-AT GTT AAT GGT ATT GGT GCA GATGAACAAGGT AAAACTGAA TTA CCA AAA -3'

IcdV-16:       5' p-GCA TTA TTA GAT GAT GCA TTT ATT TGT GTTGATCAT CCA  GGT CAA GCA CG-3'

IcdV-17:       5' p-T GCA GAA GGT GAA TTT CAACAA TTACCAGATCGTGAA TTA GGT CCA TCT T-3'

IcdV-18:       5' p-TA GCA GAT TTA TGT GCAGCACCAGAA  ATT  GCA GCACCACAT CCA GAA CGT-3'

IcdV-19:       5' p-TTA TCT GTT TTTGATTCTACT  GGT TCT GCA TTT  GCA GAT C ATATTGCA TTA GAT  GTTTTATTA-3'

IcdV-20:       5' p-GGT TTT  GCA GAT GAA TTA GGT TTA GGT CAT AAAATGTCTATT  GAAT-3'

IcdV-21:       5' p-CTACT  CCA GAA GAT GTT TTA GAT CCA TAT TCT  TTATAATAAAGATCTA-3'

"Antisense" strand:

IcdVrev-1:     5' p-AGCTTAGATCTTTATTATAAAGAATATGGATCTAAAACATCTTCTGGAGTAGATT CAATA GACATTTTATGAC-3'

IcdVrev-2:     5' p-CTAAACCTAATTCATCTGCAAAACCTAATAAAACATCTAATGCAATATGA-3'

IcdVrev-3:     5' p-TCTGCAAATGCAGAACCAGTAGAATCAAAAACAGATAAACGTTCTGGATG-3'

IcdVrev-4:     5' p-TGGTGCTGCAATTTCTGGTGCTGCACATAAATCTGCTAAAGATGGACCT-3'

IcdVrev-5:     5' p-AATTCACGATCTGGTAATTGTTGAAATTCACCTTCTGCACGTGCTTGACCT-3'

IcdVrev-6:     5' p-GGATGATCAACACAAATAAATGCATCATCTAATAATGCTTTTGGTAATT-3'

IcdVrev-7:     5' p-CAGTTTTACCTTGTTCATCTGCACCAATACCATTAACATGTAAATGTGCTT-3'

IcdVrev-8:     5' p-GACGTGGTTCTGCTGGAACAACTGGACCACCACCAACTGGAACAGAAGTAACAGTACATAAAACATCTGCA-3'

EXAMPLE 5

Overexpression of the Gene pipA* in *Escherichia coli*

The gene pipA* was cloned in the vector pQE60 (QIAGEN) (plasmid of which the coding sequences were previously modified as indicated above), between the restriction sites NcoI and HindIII on the basis of the plasmid pSP43 constructed in Example 3. The resulting plasmid pSP47 was introduced into a strain of *E. coli* K12 MG1655 (Vidal et al., 1998) expressing the gene lacI on the basis of the auxiliary plasmid pREP4 (QIAGEN). The strain +75 thus obtained was cultivated in the LB medium and the expression of the gene pipA* was induced by the addition of IPTG according to the supplier's instructions. The total proteins of the cells were separated by polyacrylamide/SDS gel electrophoresis and stained with Coomassie blue. A protein with the molecular weight of 36 kD was detected and its rate of expression was estimated at approximately 5% of total proteins.

EXAMPLE 6

Overexpression of the Genes pipA, rapL, rapL* and rapL** in *Escherichia coli*

Proceeding as described in Example 5, a strain of *E. coli* overexpressing the gene pipA (strain +353) was obtained by introducing the plasmid pKT37. This plasmid was obtained from the plasmid pKT36 described in Example 1 by cloning of the gene of interest between the restriction sites NcoI and HindIII of the vector pQE60.

Similarly, strains of *E. coli* overexpressing the genes rapL (strain +38), rapL* (strain +60) or rapL** (strain +73) were obtained by introducing respectively the plasmids pSP32, pSP37 or pSP45. These plasmids pSP32, pSP37 or pSP45 were obtained respectively from the plasmids pKT30, pSP33 or pSP36, described in Examples 2 and 4, by cloning of the gene of interest between the restriction sites SphI and HindIII of the vector pQE70.

The rate of expression of these different proteins was determined as described in Example 5. For each strain, a protein with the expected molecular weight was detected with an expression rate of approximately 5% of total proteins.

EXAMPLE 7

Amplification by PCR and Overexpression of the ocd Gene of *Agrobacterium tumefaciens* in *Eschericia coli*

A preparation of the plasmid Ti-C58 of *Agrobacterium tumefaciens* CIP 104333 was produced as described elsewhere (Hayman et al., *Mol. Gen. Genet.*, 223, (1990), 465-473). The ocd gene (Sans et al., (1988), ibid) was amplified by PCR from this preparation of the plasmid Ti-C58.

The reaction was carried out in a volume of 50 pL of buffer 20 mM Tris-HCl pH 8.8 containing 10 mM KCl, 10 mM $(NH_4)_2SO_4$, 2 mM $MgSO_4$, 0.1% Triton X-100, 2 ng of the µplasmid Ti-C58, 200 µM of each of the four dNTP, 1 unit of Vent DNA Polymerase (BioLabs), and 500 nM of each of the following two oligodeoxynucleotides:

5' CCCGCATGCCTGCACTTGCCAACC (SEQ ID NO: 87)

5' CCCAGATCTTAACCACCCAAACGTCGGAAA (SEQ ID NO: 88)

The PCR procedure applied began by a step of denaturation at 94° C. for 2 minutes followed by 30 cycles characterised by a sequence of 30 seconds of denaturation at 94° C., followed by 30 seconds of hybridisation at 52° C., then 1 minute 30 seconds of elongation at 72° C. The procedure is completed by a step of elongation at 72° C. for 10 minutes.

The fragment thus amplified was digested by NcoI and BglII and cloned in the previously cut vector pQE70 (QIAGEN) (plasmid of which the coding sequences have been previously modified as indicated above). The fragment NcoI and BglII of the plasmid pKR7 thus obtained was sequenced. The specified protein differs by two amino acids relative to the published sequence (Sans et al., (1988), ibid), namely the residue Gln212 replaced by lysine and the residue Ile297 replaced by leucine. The two deviations were confirmed by sequencing of a product of amplification by PCR obtained independently.

By proceeding as described in Example 5, a strain of *E. coli* overexpressing the ocd gene (strain +78) was obtained by introducing the plasmid pKR7. The rate of expression of the protein coded by the ocd gene was determined as described in Example 5. A protein with a molecular weight conforming to that which was expected was detected with a rate of expression of approximately 5% of the total proteins.

EXAMPLE 8

Production of L-pipecolic Acid from L-lysine by Cellular Suspensions of the Recombinant Strains of *E. coli*

The strain +75 constructed in Example 5 is cultivated in the mineral medium MS (Richaud, et al., *J. Biol. Chem.*, 268, (1993), 26827-35) containing 2 g/L glucose, 50 mg/L ampicillin and 30 mg/L kanamycin. At the end of 14 hours of culture, 400 mL of mineral medium MS containing 2 g/L glucose are inoculated at 1/10 with the preculture of the strain +75. This culture is placed at 37° C. with stirring until an $OD_{600\,nm}$ of 0.7 is reached. The gene pipA* is then induced for 4 hours at 37° C. by the addition of 1 mM of IPTG to 200 mL of culture. A reference culture of 200 mL without the addition of IPTG is also produced. At the end of this step, the two cultures are centrifuged at 13000 g and the cellular pellets are taken up in mineral medium MS in such a way as to concentrate the cells 100 times. The cells are then permeabilised by two steps of freezing/thawing at −20° C. favouring the access of the substrate to the enzyme. L-lysine monohydrochloride (pH=7) is then added at a final concentration of 1 M in the cellular suspensions (final volume=2 mL). The enzymatic reaction is effected at 37° C. with stirring. At the end of 20 hours a sample of 300 µL of each culture is taken which is centrifuged at 13000 g in such a way as to recover the supernatant. A dilute solution of the supernatants is then deposited on a thin layer of silica and simultaneously analysed with HPLC.

A compound with chromatographic migration (Rf=0.22; eluant: butanol/acetic acid/water 4/1/1 in CMC) and stained by ninhydrin which are indistinguishable from those of L-pipecolic acid is detected in the case of the culture induced with IPTG and absent in the case of the non-induced reference culture.

The analysis with HPLC (conditions described below) indicates a concentration of 40 g/L of L-pipccolate at the end of 20 hours. The enantiomeric excess is greater than 95%.

Tests of production of L-pipecolic. acid from L-lysine were carried out with the strains +38, +60, +73, +78 and +353 constructed in Examples 6 and 7, under the same conditions as those applied above for the strain +75. The analysis by chromatography of the respective supernatants on a thin silica layer after staining with ninhydrin revealed a production of L-pipecolic acid only with the strains +73, +78 and +353.

Description of the HPLC Method Used:
   Phenomenex Synergi Polar-RP-80 4µ (250×4.6 mm) column thermostat-controlled at 30° C.,
   UV Detection at 210 mn
   Volume of sample injected: 10 µL
   Isocratic elution by a solution of 0.05% of TFA in water for 5 minutes followed by washing of the column with 80% acetonitrile and 0.05% TFA in water,
   Retention time: lysine 2.98 minutes and pipecolic acid 4.62 minutes.

EXAMPLE 9

Production of L-thiomorpholine-2-carboxylic Acid from L-thialysine

The production of L-thiomorpholine-2-carboxylic acid was carried out on the basis of a cellular suspension of the strain +75 prepared as described in Example 8. L-thialysine (S-(2-aminoethyl)-L-cysteine) (SIGMA) is added at a final concentration of 1 M. Thin silica layer chromatography of the supernatant of the incubated suspension is carried out and it reveals a compound with migration (Rf=0.28; eluant: butanol/acetic acid/water 4/1/1) and stained by ninhydrin which are distinct from those of L-thialysine and L-pipecolic acid.

Under the same conditions, the strain +78 described in Example 7 produces a compound identical to that produced by the strain +75.

EXAMPLE 10

Production of a Mixture of 5-R- and 5-S-hydroxy-L-pipecolic Acids from a Mixture of L- and D-5-(R,S) hydroxylysine The production of a mixture of 5-R- and 5-S-hydroxy-L-pipecolic acids was carried out on the basis of a cellular suspension of the strain +75 prepared as described in Example 8. 5-R,S-hydroxy-D,L-lysine (SIGMA) is added at a final concentration of 1 M. Thin silica layer chromatography of the supernatant of the incubated suspension is carried out and it reveals two compounds present in equivalent proportions with migration ($Rf_1$=0.14, $Rf_2$=0.20; eluant: butanol/acetic acid/water 4/1/1) and stained by ninhydrin which are distinct from those of 5-R,S-hydroxy-D,L-lysine and L-pipecolic acid.

Under the same conditions, the strain +78 described in Example 7 produces two compounds identical to those produced by the strain +75.

EXAMPLE 11

Preparation of Other Cyclic Amino Acids

The great versatility of the method according to the present invention can be illustrated by the following cyclic amino acids, obtained using the mode of operation described in Example 8 by modifying the nature of the starting diamino acid:

| L-diamino acid | Cyclic L-amino acid |
| --- | --- |
| 2,6-diaminoheptanedioic acid | Piperidine-2,6-heptanedioic acid |
| 2,6-diamino-5-hydroxyhexanoic acid | 5-hydroxypiperidine-2-carboxylic acid |
| 2-amino-3-(2-aminoethylsulphanyl)propanoic acid | Thiomorpholine-3-carboxylic acid |
| Azalysine (βN-2-aminoethyl-α,β-diaminopropionic acid | Piperazine-2-carboxylic acid |

The invention claimed is:

1. A method of production of a cyclic L-amino acid of formula (I) or a salt or derivative thereof:

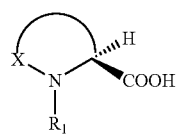

(I)

wherein said method comprises:
(a) expressing a polynucleotide sequence selected from the group consisting of: a polynucleotide sequence comprising SEQ ID NO: 1, a polynucleotide sequence comprising SEQ ID NO: 2, and a polynucleotide sequence comprising SEQ ID NO:5; wherein SEQ ID NOs:1,2 and 5 are generated by mutagenesis and encode ornithine cyclodeaminase enzyme, and wherein the encoded ornithine cyclodeaminase enzyme is produced in a recombinant E.coli strain;
(b) reacting an L-diamino acid of formula (II)

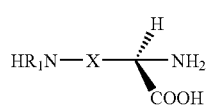

(II)

a salt or derivative of an L-diamino acid of formula (II), or an enantiomeric mixture comprising an L-diamino acid of formula (II) and a corresponding D-diamino acid, the salts or derivatives thereof in variable proportions, with the produced enzyme of step (a); and
(c) recovering the cyclic L-amino acid of formula (I) or a salt or derivative thereof in an enantiomeric excess of at least 80%; wherein:

$R_1$ in formula (I) and formula (II) is selected from the group consisting of: a hydrogen atom, a linear or branched alkyl radical having from 1 to 6 carbon atoms and a linear or branched acyl radical having from 1 to 6 carbon atoms;

X in formula (I) and formula (II) represents a saturated, or partially or totally unsaturated, linear or branched $C_1$-$C_9$ hydrocarbon chain, optionally comprising in the chain and/or at the end of the chain one or several heteroatoms or heterogroups selected from the group consisting of: O, S, P, and $NR_2$;

$R_2$ represents H or $C_1$-$C_4$ alkyl or acyl group;

the hydrocarbon chain is optionally being substituted by one or several identical or different radicals selected from the group consisting of: —R, —O R, —SR, =O, —C(O)OR, —C(S)OR, —C(O)NR'R", —C(S)NR'RR", —CN, —N $O_2$, —NR'R", —NR'C(O)R, —SiOR and -SiOR;

R, R', and R", are identical or different and represent hydrogen or a linear or branched, saturated, or totally or partially unsaturated, hydrocarbon radical having from 2 to 20 carbon atoms; and R' and R" optionally form a ring with the atom carrying them.

2. The method of claim 1, wherein the compound of formula (I) comprises a ring with six bonds, X representing a hydrocarbon chain with four bonds.

3. Method of claim 1, wherein X represents a linear or branched alkylene chain.

4. The method of claim 1, wherein the expression product of step (a) is purified prior to step (b).

5. The method of claim 1, wherein the compound of general formula (I) is in the form of an ammonium salt in aqueous solution.

6. The method of claim 1, wherein L-piperidine-2-carboxylic acid or one of its salts is prepared from L-lysine.

7. The method of claim 1, wherein L-piperazine-2-carboxylic acid or one of its salts is prepared from L-azalysine.

8. The method of claim 1, wherein L-thiomorpholine-2-carboxylic acid or one of its salts is prepared from L-thialysine.

9. The method of claim 1, wherein X in formula (I) and formula (II) represents a saturated, or partially or totally unsaturated, linear or branched $C_2$-$C_4$ hydrocarbon chain, optionally comprising in the chain and/or at the end of the chain one or several heteroatoms or heterogroups selected from the group consisting of: O, S, P, and $NR_2$.

10. Method of claim 1, wherein no exogenous nicotinamide adenine dinucleotide (NAD) is added to the reaction medium.

* * * * *

SEQUENCE LISTING

```
<160> NUMBER OF SEQ ID NOS: 5

<210> SEQ ID NO 1
<211> LENGTH: 1097
<212> TYPE: DNA
<213> ORGANISM: Artificial Sequence
<220> FEATURE:
<223> OTHER INFORMATION: nucleic sequence of the synthetic gene pipA*

<400> SEQUENCE: 1
gaattcgagg ttccatggaa acttgggttt taggtcgtcg tgatgttgca gaagttgttg      60
cagcagttgg tcgtgatgaa ttaatgcgtc gtattatcga tcgtttaact ggtggtttag     120
cagaaattgg tcgtggtgaa cgtcatttat ctccattacg tggtggttta gaacgttctg     180
aaccagttcc aggtatttgg gaatggatgc cacatcgtga accaggtgat catattactt     240
taaaaactgt tggttattct ccagcaaatc caggtcgttt tggtttacca actattttag     300
gtaccgttgc acgttatgat gatactactg gtgcattaac tgcattaatg gatggtgttt     360
tattaactgc attacgtact ggtgcagcat ctgctgttgc atctcgtttta ttagcacgtc     420 cagattctca tactttaggt ttaattggta ctggtgcaca agcagttact caattgcatg     480
cattatcttt agttttacca ttacaacgtg cattagtttg ggatactgat ccagcacatc     540
gtgaatcttt tgcacgtcgt gcagcattta ctggtgtttc tgttgaaatt gcagaaccag     600
cacgtattgc agcagaagca gatgttattt ctactgcaac ttctgttgca gttggtcaag     660
gtccagtttt accagatact ggtgttcgtg aacatttaca tattaatgca gttggtgcag     720
atttagttgg taaaactgaa ttaccattag gtttattaga acgtgcattt gttactgcag     780
```

-continued

```
atcatccaga acaagcatta cgtgaaggtg aatgtcaaca attatctgct gatcgtttag      840
gtccacaatt agcacattta tgtgcagatc cagcagcagc agcaggtcgt caagatactt      900
tatctgtttt tgattctact ggttttgcat ttgaagatgc attagcaatg gaagtttttt      960
tagaagcagc agcagaacgt gatttaggta ttcgtgttgg tattgaacat catccaggtg     1020
atgcattaga tccatatgca ttacaaccat taccattacc attagcagca ccagcacatt     1080
aataaagatc taagctt                                                    1097
```

<210> SEQ ID NO 2
<211> LENGTH: 1061
<212> TYPE: DNA
<213> ORGANISM: Artificial Sequence
<220> FEATURE:
<223> OTHER INFORMATION: nucleic sequence of the synthetic gene rapL*

<400> SEQUENCE: 2

```
gaattcgagg ttgcatgcaa actaaagttt tatgtcaacg tgatattaaa cgtattttat       60
ctgttgttgg tcgtgatgtt atgatggatc gtttaatttc tgaagttcat gcaggttttg      120
cacgtttagg tcgtggtgaa actgatgaac caccaccacg tccaggtttt gcacgtggtg      180
gtgatgttcc aggtgttatt gaatttatgc cacatcgtgc atctggtatt ggtgttacta      240
tgaaaactgt ttcttattct ccagaaaatt ttgaacgttt taatttacca actattgttg      300
gtaccgtttc tcgtttaggt gatgattctg ttctatggt tgcattagca gatgcagcaa       360
ctattactgc aatgcgtact ggtgcagttg catctgttac tactcgttta ttagcacgtc      420
caggttctac tactttagca ttaattggtg caggtgcaca agcagttact caagcacatg      480
cattatctcg tgttttacca ttagaacgta ttttaatttc tgatattaaa gcagaacatg      540
cagaatcttt tgcaggtcgt gttgcatttt tagaattacc agttgaagtt actgatgcag      600
caactgcaat ggcaactgca gatgttttat gtactgttac ttctgttcca gttggtggtg      660
gtccagttgt tccagcagaa ccacgtcaag cacatttaca tgttaatggt attggtgcag      720
atgaacaagg taaaactgaa ttaccaaaag cattattaga tgatgcattt atttgtgttg      780
atcatccagg tcaagcacgt gcagaaggtg aatttcaaca attaccagat cgtgaattag      840
gtccatcttt agcagattta tgtgcagcac cagaaattgc agcaccacat ccagaacgtt      900
tatctgtttt tgattctact ggttctgcat ttgcagatca tattgcatta gatgttttat      960
taggttttgc agatgaatta ggtttaggtc ataaaatgtc tattgaatct actccagaag     1020
atgtttagaa tccatattct ttataataaa gatctaagct t                         1061
```

<210> SEQ ID NO 3
<211> LENGTH: 355
<212> TYPE: PRT
<213> ORGANISM: Streptomyces pristinaespiralis
<220> FEATURE:
<221> NAME/KEY: PROPEP
<222> LOCATION: (1)...(355)
<223> OTHER INFORMATION: Protein sequence of the gene pipA

<400> SEQUENCE: 3

```
Met Glu Thr Trp Val Leu Gly Arg Arg Asp Val Ala Glu Val Val Ala
 1               5                  10                  15

Ala Val Gly Arg Asp Glu Leu Met Arg Arg Ile Ile Asp Arg Leu Thr
            20                  25                  30

Gly Gly Leu Ala Glu Ile Gly Arg Gly Glu Arg His Leu Ser Pro Leu
        35                  40                  45
```

```
Arg Gly Gly Leu Glu Arg Ser Glu Pro Val Pro Gly Ile Trp Glu Trp
 50                  55                  60

Met Pro His Arg Glu Pro Gly Asp His Ile Thr Leu Lys Thr Val Gly
 65                  70                  75                  80

Tyr Ser Pro Ala Asn Pro Ala Arg Phe Gly Leu Pro Thr Ile Leu Gly
                 85                  90                  95

Thr Val Ala Arg Tyr Asp Asp Thr Thr Gly Ala Leu Thr Ala Leu Met
            100                 105                 110

Asp Gly Val Leu Leu Thr Ala Leu Arg Thr Gly Ala Ala Ser Ala Val
            115                 120                 125

Ala Ser Arg Leu Leu Ala Arg Pro Asp Ser His Thr Leu Gly Leu Ile
    130                 135                 140

Gly Thr Gly Ala Gln Ala Val Thr Gln Leu His Ala Leu Ser Leu Val
145                 150                 155                 160

Leu Pro Leu Gln Arg Ala Leu Val Trp Asp Thr Asp Pro Ala His Arg
                165                 170                 175

Glu Ser Phe Ala Arg Arg Ala Ala Phe Thr Gly Val Ser Val Glu Ile
            180                 185                 190

Ala Glu Pro Ala Arg Ile Ala Ala Glu Ala Asp Val Ile Ser Thr Ala
            195                 200                 205

Thr Ser Val Ala Val Gly Gln Gly Pro Val Leu Pro Asp Thr Gly Val
    210                 215                 220

Arg Glu His Leu His Ile Asn Ala Val Gly Ala Asp Leu Val Gly Lys
225                 230                 235                 240

Thr Glu Leu Pro Leu Gly Leu Glu Arg Ala Phe Val Thr Ala Asp
                245                 250                 255

His Pro Glu Gln Ala Leu Arg Glu Gly Glu Cys Gln Gln Leu Ser Ala
                260                 265                 270

Asp Arg Leu Gly Pro Gln Leu Ala His Leu Cys Ala Asp Pro Ala Ala
            275                 280                 285

Ala Ala Gly Arg Gln Asp Thr Leu Ser Val Phe Asp Ser Thr Gly Phe
    290                 295                 300

Ala Phe Glu Asp Ala Leu Ala Met Glu Val Phe Leu Glu Ala Ala Ala
305                 310                 315                 320

Glu Arg Asp Leu Gly Ile Arg Val Gly Ile Glu His His Pro Gly Asp
                325                 330                 335

Ala Leu Asp Pro Tyr Ala Leu Gln Pro Leu Pro Leu Pro Leu Ala Ala
            340                 345                 350

Pro Ala His
    355

<210> SEQ ID NO 4
<211> LENGTH: 343
<212> TYPE: PRT
<213> ORGANISM: Streptomyces hygroscopicus
<220> FEATURE:
<221> NAME/KEY: PROPEP
<222> LOCATION: (1)...(343)
<223> OTHER INFORMATION: Protein sequence of the gene rapL

<400> SEQUENCE: 4

Met Gln Thr Lys Val Leu Cys Gln Arg Asp Ile Lys Arg Ile Leu Ser
 1                   5                  10                  15

Val Val Gly Arg Asp Val Met Met Asp Arg Leu Ile Ser Glu Val His
             20                  25                  30

Ala Gly Phe Ala Arg Leu Gly Arg Gly Glu Thr Asp Glu Pro Pro Pro
```

```
                35                  40                  45
Arg Thr Gly Phe Ala Arg Gly Gly Asp Val Pro Gly Val Ile Glu Phe
 50                  55                  60

Met Pro His Arg Ala Ser Gly Ile Gly Val Thr Met Lys Thr Val Ser
 65                  70                  75                  80

Tyr Ser Pro Gln Asn Phe Glu Arg Phe Asn Leu Pro Thr Ile Val Gly
                 85                  90                  95

Thr Val Ser Arg Leu Asp Asp Asp Ser Gly Ser Met Val Ala Leu Ala
                100                 105                 110

Asp Ala Ala Thr Ile Thr Ala Met Arg Thr Gly Ala Val Ala Ala Val
                115                 120                 125

Ala Thr Arg Leu Leu Ala Arg Pro Gly Ser Thr Thr Leu Ala Leu Ile
130                 135                 140

Gly Ala Gly Ala Gln Ala Val Thr Gln Ala His Ala Leu Ser Arg Val
145                 150                 155                 160

Leu Pro Leu Glu Arg Ile Leu Ile Ser Asp Ile Lys Ala Glu His Ala
                165                 170                 175

Glu Ser Phe Ala Gly Arg Val Ala Phe Leu Glu Leu Pro Val Glu Val
                180                 185                 190

Thr Asp Ala Ala Thr Ala Met Ala Thr Ala Asp Val Leu Cys Thr Val
                195                 200                 205

Thr Ser Val Pro Val Gly Gly Gly Pro Val Val Pro Ala Glu Pro Arg
210                 215                 220

Gln Ala His Leu His Val Asn Gly Ile Gly Ala Asp Glu Gln Gly Lys
225                 230                 235                 240

Thr Glu Leu Pro Lys Ala Leu Leu Asp Asp Ala Phe Ile Cys Val Asp
                245                 250                 255

His Pro Gly Gln Ala Arg Ala Glu Gly Glu Phe Gln Gln Leu Pro Asp
                260                 265                 270

Arg Glu Leu Gly Pro Ser Leu Ala Asp Leu Cys Ala Ala Pro Glu Ile
                275                 280                 285

Ala Ala Pro His Pro Glu Arg Leu Ser Val Phe Asp Ser Thr Gly Ser
290                 295                 300

Ala Phe Ala Asp His Ile Ala Leu Asp Val Leu Leu Gly Phe Ala Asp
305                 310                 315                 320

Glu Leu Gly Leu Gly His Lys Met Ser Ile Glu Ser Thr Pro Glu Asp
                325                 330                 335

Val Leu Asp Pro Tyr Ser Leu
                340

<210> SEQ ID NO 5
<211> LENGTH: 1061
<212> TYPE: DNA
<213> ORGANISM: Artificial Sequence
<220> FEATURE:
<223> OTHER INFORMATION: nucleic sequence of the synthetic gene rapL**

<400> SEQUENCE: 5
gaattcgagg ttgcatgcaa actaaagttt tatgtcaacg tgatattaaa cgtatttttat      60 ctgttgttgg tcgtgatgtt atgatggatc gtttaatttc tgaagttcat gcaggttttg     120
cacgtttagg tcgtggtgaa actgatgaac caccaccacg tactggtttt gcacgtggtg     180
gtgatgttcc aggtgttatt gaatttatgc cacatcgtgc atctggtatt ggtgttacta     240
tgaaaactgt ttcttattct ccacaaaatt ttgaacgttt taatttacca actattgttg     300
```

-continued

```
gtaccgtttc tcgtttagat gatgattctg gttctatggt tgcattagca gatgcagcaa    360
ctattactgc aatgcgtact ggtgcagttg cagcagttgc aactcgttta ttagcacgtc    420
caggttctac tactttagca ttaattggtg caggtgcaca agcagttact caagcacatg    480
cattatctcg tgttttacca ttagaacgta ttttaatttc tgatattaaa gcagaacatg    540
cagaatcttt tgcaggtcgt gttgcatttt tagaattacc agttgaagtt actgatgcag    600
caactgcaat ggcaactgca gatgttttat gtactgttac ttctgttcca gttggtggtg    660
gtccagttgt tccagcagaa ccacgtcaag cacatttaca tgttaatggt attggtgcag    720
atgaacaagg taaaactgaa ttaccaaaag cattattaga tgatgcattt atttgtgttg    780
atcatccagg tcaagcacgt gcagaaggtg aatttcaaca attaccagat cgtgaattag    840
gtccatcttt agcagattta tgtgcagcac cagaaattgc agcaccacat ccagaacgtt    900
tatctgtttt tgattctact ggttctgcat ttgcagatca tattgcatta gatgttttat    960
taggttttgc agatgaatta ggtttaggtc ataaaatgtc tattgaatct actccagaag   1020 atgtttaga tccatattct ttataataaa gatctaagct t                        1061
```